United States Patent [19]
Holt et al.

[11] Patent Number: 6,042,679
[45] Date of Patent: *Mar. 28, 2000

[54] METHOD FOR TREATING DAMAGED FINGERNAILS

[76] Inventors: Diannamarie T. Holt, 1721 Windrose Ln., Santa Rosa, Calif. 95403; Michael J. Levin, 1736 S. Clear Creek Pl., Danville, Calif. 94526

[*] Notice: This patent issued on a continued prosecution application filed under 37 CFR 1.53(d), and is subject to the twenty year patent term provisions of 35 U.S.C. 154(a)(2).

[21] Appl. No.: 09/047,764

[22] Filed: Mar. 24, 1998

Related U.S. Application Data

[62] Division of application No. 07/790,561, Nov. 12, 1991, abandoned.

[51] Int. Cl.[7] .............................. B32B 31/04; A45D 31/00
[52] U.S. Cl. ......................... 156/249; 156/248; 156/265; 156/268; 132/73
[58] Field of Search ................................. 156/248, 249, 156/268, 265; 132/73; 206/460, 527, 823; 424/61, 401

[56] References Cited

U.S. PATENT DOCUMENTS

| | | |
|---|---|---|
| 2,209,408 | 7/1940 | Litt . |
| 2,288,386 | 6/1942 | Belden . |
| 2,413,537 | 12/1946 | Aberbach . |
| 2,581,982 | 1/1952 | Terry .......................................... 132/73 |
| 2,633,139 | 3/1953 | Pettey ......................................... 132/73 |
| 2,746,460 | 5/1956 | Jellinek ...................................... 132/73 |
| 2,764,166 | 9/1956 | Bogoslowsky ............................. 132/73 |
| 2,864,384 | 12/1958 | Walter ........................................ 132/73 |
| 2,941,535 | 6/1960 | Lappe . |
| 3,023,887 | 3/1962 | Cohen ....................................... 132/73 |
| 3,037,514 | 6/1962 | Lappe . |
| 3,228,404 | 1/1966 | Turner ....................................... 132/73 |
| 3,478,756 | 11/1969 | Sautter et al. . |
| 3,483,289 | 12/1969 | Michaelson et al. . |
| 3,552,401 | 1/1971 | Michaelson et al. . |
| 3,645,835 | 2/1972 | Hodgson ................................. 132/73 X |
| 3,898,357 | 8/1975 | Miller et al. ............................ 132/73 X |
| 4,140,139 | 2/1979 | Aylott ......................................... 132/73 |
| 4,536,426 | 8/1985 | Massey ................................... 132/73 X |
| 4,824,702 | 4/1989 | Straub ..................................... 132/73 X |
| 4,903,840 | 2/1990 | So ........................................... 132/73 X |
| 4,913,173 | 4/1990 | Hokama et al. .......................... 132/73 |
| 4,943,462 | 7/1990 | Komerska et al. ..................... 132/73 X |
| 4,954,190 | 9/1990 | Taeckens ................................ 132/73 X |
| 5,146,935 | 9/1992 | Rumore et al. ........................... 132/73 |
| 5,415,903 | 5/1995 | Hoffman et al. ....................... 132/73 X |
| 5,525,389 | 6/1996 | Hoffman et al. ....................... 132/73 X |
| 5,791,482 | 8/1998 | Murphy et al. ........................ 132/73 X |

FOREIGN PATENT DOCUMENTS

| | | |
|---|---|---|
| 88/05896 | 6/1990 | Brazil . |
| 90/01941 | 11/1991 | Brazil . |
| 2 241 272 | 4/1975 | France . |
| 2 493 116 | 5/1982 | France . |
| 33 37 458 | 4/1985 | Germany . |
| 8-238121 | 9/1996 | Japan . |
| 88/02227 | 4/1988 | WIPO . |
| 94/06322 | 3/1994 | WIPO . |

*Primary Examiner*—Curtis Mayes
*Attorney, Agent, or Firm*—Herbert C. Schulze

[57] ABSTRACT

A method and apparatus for treating damaged fingernails which includes the use of a sheet of transparent vinyl film coated on one side with an adhesive suitable to adhere to a fingernail, wherein a multiplicity of generally oval shaped forms and into a backing material to which the adhesive adheres releasable in such manner that an individual oval vinyl repair item may be peeled from the backing strip and placed upon a damaged fingernail and wherein the same material may be used in reverse in such manner that the adhesive material will be exposed before the item is removed from the backing strip and the fingernail may be pressed against the adhesive so as to facilitate the placing and removal of the protective vinyl on the fingernail.

1 Claim, 2 Drawing Sheets

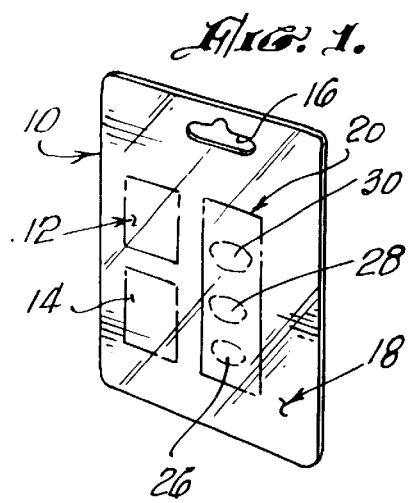
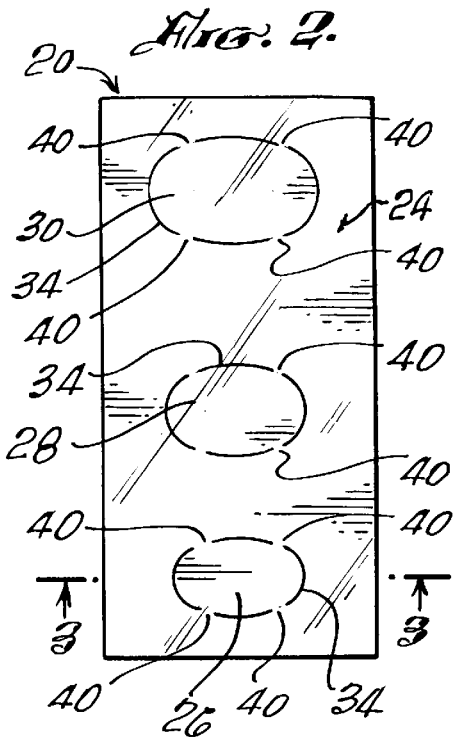
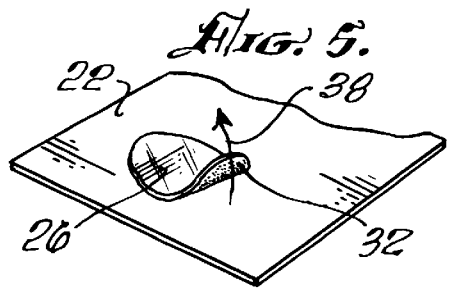
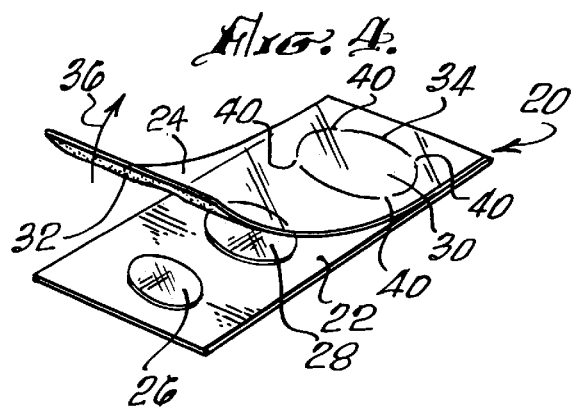
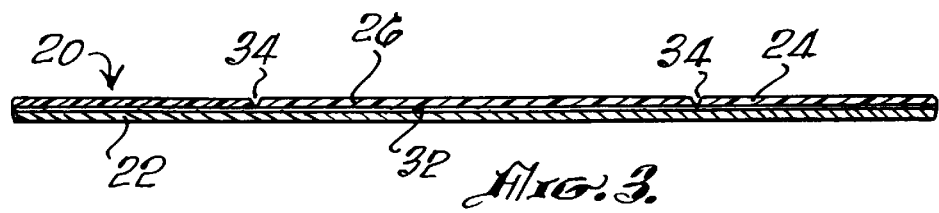

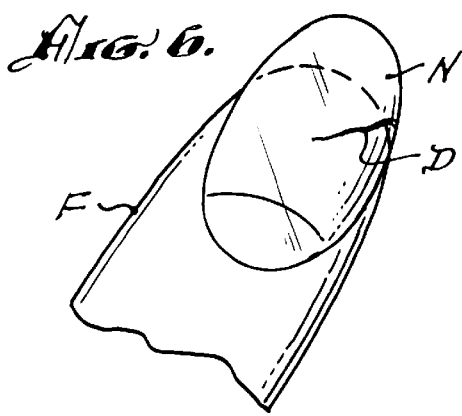
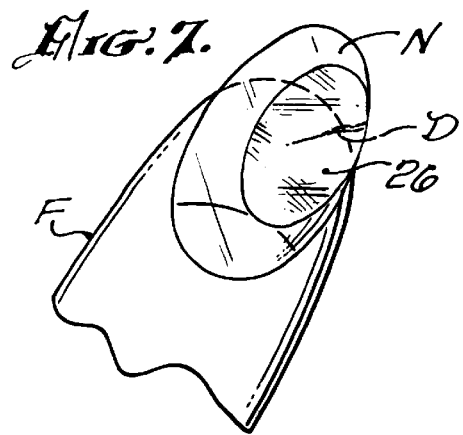
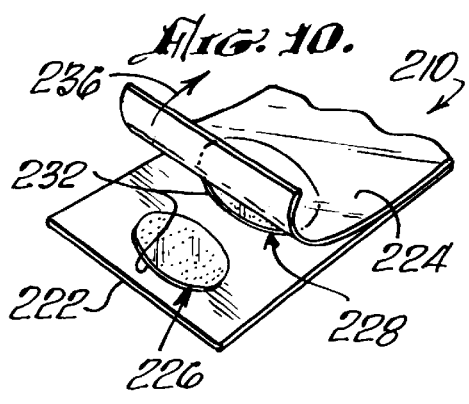
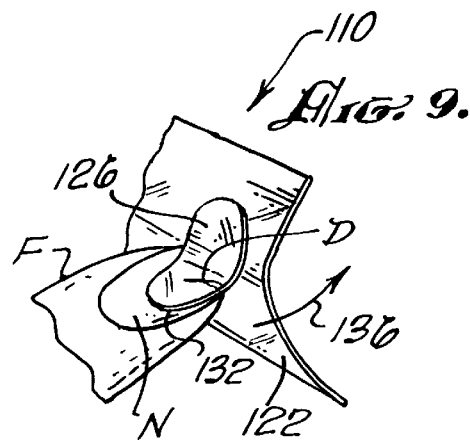
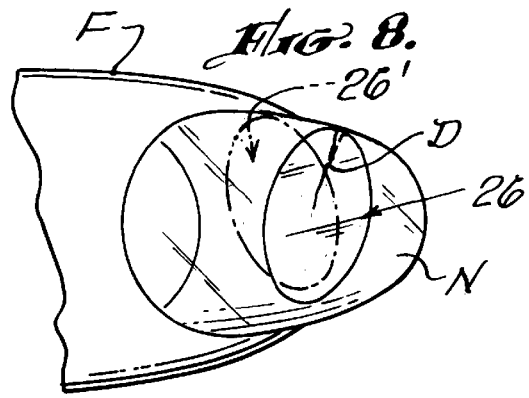

METHOD FOR TREATING DAMAGED FINGERNAILS

CROSS REFERENCE TO RELATED PATENT APPLICATIONS

This application is related to, and is a division of, our application Ser. No. 07/790,561 filed Nov. 12, 1991, now abandoned.

BACKGROUND OF THE INVENTION

I. Field of the Invention

This invention is in the general field of treating and caring for damaged fingernails or the like.

The invention is even more particularly directed to a covering for a damaged fingernail or the like.

The invention is even more particularly directed to a method of applying a covering to a damaged fingernail or the like and the method of treating damaged fingernails in general.

II. Description of the Prior Art

In the past when one has had a damaged fingernail it has either been left unattended or has been covered by a conventional, existing material such as a bandaid, adhesive tape, transparent adhesive tape, an artificial fingernail, adhesive material, or the like.

We know of no prior art wherein a properly shaped pre-cut material has been used or obtainable. In that sense there is no prior art. Further, there has been no suggestion in the past of the use of a clear vinyl material for this purpose. Although such vinyl materials are available for other purposes, it appears that this is a unique use for such material. In this sense, further, there is no prior art.

SUMMARY OF THE INVENTION

It is quite common for individuals to have a break, or crack in a fingernail or a toenail. Such is uncomfortable and can lead to infection and even possibly the tearing of the fingernail or toenail from the finger or toe leaving raw flesh. In general when one suffers from a damaged nail it will be temporarily ignored, or cured with the application of a bandaid or some type of adhesive material or the like. These repairs are generally unsatisfactory, can lead to infection. Such repairs frequently are difficult to remove as well.

We have been studying the field of nail repair for some time. We have conceived and developed a convenient, inexpensive and unique method and apparatus for dealing with such problems.

We have perfected a thin transparent vinyl patch with one side coated with a pressure sensitive adhesive suitable to adhere to a nail. We have devised a method and apparatus for easily storing and displaying the patch in package form. We have provided a sheet of material which has a choice of a number of sizes of the patch, contoured in such a manner so that each patch is aesthetic in appearance and practical in use.

The foregoing has been accomplished after careful testing and use.

It is an object of this invention to provide a simple method and apparatus for covering a break or tear on a fingernail or the like;

It is a further object of this invention to provide a nail patch which can easily be removed after a period of time;

Another object of this invention is to provide a sheet of material containing a plurality of nail patches, from which one or more can be extracted as desired.

Another object of this invention is to provide a means for displaying the patches and for storage until the time necessary for use.

A further object of this invention is to provide a method and apparatus for protecting a damaged fingernail during healing without danger of infection.

The foregoing and other objects and advantages of this invention will become apparent to those skilled in the art upon reading the description of a preferred embodiment, which follows, in conjunction with a review of the appended figures.

BRIEF DESCRIPTION OF THE DRAWINGS

FIG. 1 is a perspective of a pre-packaged display packet of material suitable to practice the method of this invention;

FIG. 2 is an enlarged plan view of a sheet of material removed from the display packet and ready for use;

FIG. 3 is an enlarged cross section of the sheet of FIG. 2 as it is viewed along line 3—3 of FIG. 2.

FIG. 4 is a perspective of the sheet of FIG. 2 showing the top layer being peeled away from a lower layer;

FIG. 5 is a fragmentary perspective of a portion of FIG. 4 wherein a patch is shown being peeled away from the lower backing strip;

FIG. 6 is a fragmentary perspective of a finger with a fingernail that has been damaged;

FIG. 7 is similar to FIG. 6 showing a patch of this invention in place over a tear or break in a damaged fingernail;

FIG. 8 is a fragmentary plan view showing the patch applied to a break in the fingernail, and in phantom lines indicating more than one patch may be used, if necessary;

FIG. 9 is a fragmentary perspective of a first alternate embodiment of the invention showing the manner of applying the patch of the invention; and FIG. 10 is a fragmentary perspective of a second alternate embodiment of the invention.

DESCRIPTION OF A PREFERRED EMBODIMENT

FIG. 1 shows a packet 10 of a type which can be displayed for sale in a retail store, or the like. Information and instructions appear at 12 and 14. An opening 16 is shown provided so the packet can be hung on conventional rack hooks, or the like. The contents of the packet can be secured by heat sealing into a plastic envelope 18.

FIGS. 2, 3, 4, and 5 show a multi-layered sheet of material 20 which is constructed by providing a sheet of backing material 22 being paper or the equivalent onto which a sheet of thin, transparent, vinyl 24 is placed. The vinyl sheet 24 is shown having patch configurations 26, 28, and 30 cut, but still in place. These configurations are preferably oval as shown.

The underside of the upper sheet 24 is coated with a thermoset acrylic pressure sensitive adhesive 32 known to those skilled in the art. The sheet 24 is mounted upon an adhesive-releasable backing sheet 22.

A cutting tool (such as a die) known to those skilled in the art, has been used to cut the individual patches 26, 28 and 30 through the vinyl but not completely through the backing sheet 22. This cut 34 is shown more clearly in FIG. 3. The cut may be, but is not necessarily, interrupted at various points 40 so that as the upper layer 24 is removed (as shown in FIG. 4) in preparing the patch for use, the patch may not be totally severed from the sheet. In this case, the patch, while held in the sheet 24, may be pressed onto the nail and then finally severed. The patch is easier to handle under certain circumstances in this manner since the entire sheet can be utilized rather than attempting to handle a small patch. In the event the item is completely cut, or even if partially severed, it may still be held on the backing sheet as indicated in FIG. 4 wherein the sheet of vinyl has been pulled away leaving only the vinyl patch 26.

FIG. 5 shows how an individual patch, such as 26, can be peeled off in the direction of arrow 38 and applied to the fingernail to cover the break or tear.

FIG. 6 shows a broken nail N with its damaged portion D. The finger F is shown in FIG. 6. The break can further develop or become infected if not attended to as set forth here.

FIG. 7 illustrates the patch 26 placed over the damaged area after the fingernail has been cleaned. If a damaged fingernail has fingernail polish, our patch will be effective and adhere properly.

An alternate method of application of a patch to a damaged fingernail is shown generally 110 in FIG. 9. Backing material 122 can be manipulated and bent in the direction of arrow 136 to allow the patch 126 to be directly placed on the fingernail N of finger F to cover the damaged point D on the fingernail.

In another alternative shown generally 210 in FIG. 10, patches 226 and 228 with the adhesive on the upward side are placed on the backing 222, the adhesive may be covered until use by an adhesive-releasable sheet 224. When the top sheet is removed, as shown in the direction of arrow 236, the user can press the nail onto the adhesive and lift the patch from the backing, already in place on the damaged nail. The finished, or exposed side of the patch when it is in place on a nail will be the side 232, which is down on the backing sheet in this illustration.

FIG. 8 illustrates in phantom line at 26 that, if necessary more than one patch may can be applied to the same nail.

The patches shown in FIG. 2 are of different sizes and the user can choose the size which will best fit the damaged nail being treated.

While the embodiments of this invention particularly shown and described are fully capable of achieving the objects and advantages desired, it is to be understood that such embodiments are for purposes of illustration only and not for purposes of limitation.

We claim:

1. The method of protecting a damaged portion of a fingernail comprising: coating a sheet of clear vinyl with a pressure sensitive adhesive; applying the sheet of vinyl to a backing material with the adhesive side against the backing material which is releasable as to the adhesive; cutting a plurality of substantially oval shapes in a multiplicity of sizes through the vinyl, but not through the backing material; packaging said vinyl material on its backing material in a package suitable to be publicly displayed and selected by customers; displaying the package; selecting the package; opening the package; selecting and removing from the package and the backing a multiplicity of oval shapes of the vinyl material, each smaller in size than the entire damaged fingernail, but sufficient in size to cover the damaged portion of the fingernail; and pressing the selected oval shaped vinyl materials to the damaged portion of the fingernail with their adhesive sides adjacent the fingernail in such manner as to cover the entire damaged portion but not the entire fingernail.

* * * * *